US008760650B2

(12) United States Patent
Palumbo

(10) Patent No.: US 8,760,650 B2
(45) Date of Patent: Jun. 24, 2014

(54) STANDARD MEDIA SUSPENSION BODY, OPTICAL PARTICULATE MEASUREMENT INSTRUMENT, AND VERIFICATION METHOD FOR AN OPTICAL PARTICULATE MEASUREMENT INSTRUMENT

(75) Inventor: Perry A. Palumbo, Fort Collins, CO (US)

(73) Assignee: Hach Company, Loveland, CO (US)

( * ) Notice: Subject to any disclaimer, the term of this patent is extended or adjusted under 35 U.S.C. 154(b) by 1053 days.

(21) Appl. No.: 12/676,642
(22) PCT Filed: Sep. 4, 2008
(86) PCT No.: PCT/US2008/075188
§ 371 (c)(1),
(2), (4) Date: Mar. 5, 2010
(87) PCT Pub. No.: WO2009/035894
PCT Pub. Date: Mar. 19, 2009

(65) Prior Publication Data
US 2010/0235133 A1  Sep. 16, 2010

Related U.S. Application Data

(60) Provisional application No. 60/971,657, filed on Sep. 12, 2007.

(51) Int. Cl.
*G01N 21/00* (2006.01)
*G01N 1/10* (2006.01)
*G01J 1/10* (2006.01)

(52) U.S. Cl.
USPC .................. 356/338; 356/246; 356/243.2

(58) Field of Classification Search
None
See application file for complete search history.

(56) References Cited

U.S. PATENT DOCUMENTS

| | | |
|---|---|---|
| 4,291,981 A | 9/1981 | Ohnishi et al. |
| 5,059,811 A | 10/1991 | King et al. |
| 5,125,747 A | 6/1992 | Sayegh et al. |
| 5,467,187 A | 11/1995 | Beers |
| 5,757,481 A | 5/1998 | O'Brien et al. |
| 5,912,737 A | 6/1999 | Bannerjee et al. |
| 6,307,630 B1 | 10/2001 | Banerjee |
| 7,180,594 B2 | 2/2007 | Williams |

FOREIGN PATENT DOCUMENTS

| | | |
|---|---|---|
| EP | 0374034 A2 | 6/1990 |
| EP | 0959353 A2 | 11/1999 |
| JP | 55129728 | 10/1980 |

OTHER PUBLICATIONS

European Search Report, Application No. EP11171411, May 16, 2012, 1 page, Munich, Germany.
Beard, Paul C., "Photoacoustic imaging of blood vessel equivalent phantoms", Proceedings of SPIE, Jan. 1, 2002, pp. 54-62, vol. 4618, XP55027094, SPIE, San Jose, California, USA.
International Search Report, Application No. PCT/US2008/075188, Mar. 9, 2009, 2 pages, EPO Office, The Netherlands.
Moffitt, T., et al., "Preparation and characterization of ployurethane optical phantoms", Journal of Biomedical Optics, vol. 11, No. 4., SPIE, Jul./Aug. 2006, 10 pages, Bellingham, WA, USA.
Zhao, Huijuan, et al., "Imaging of in vitro chicken leg using time-resolved near-infrared optical tomography", Physics in Medicine and Biology, vol. 47, Institute of Physics Publishing, IOP Publishing Ltd., 2002, pp. 1979-1993, United Kingdom.

*Primary Examiner* — Gregory J Toatley
*Assistant Examiner* — Amanda Merlino
(74) *Attorney, Agent, or Firm* — Ference & Associats LLC

(57) ABSTRACT

A standard media suspension body (150) for verification and calibration of an optical particulate measurement instrument and configured to be at least partially immersed in a sample fluid is provided according to the invention. The body (150) includes a substantially solid outer surface including a first end (151) and a second end (152) disposed along an axis of illumination A and at least one outer surface (153). The first end (151) is configured to admit impinging light. The suspension body further includes an inner volume. At least a portion of the inner volume includes a substantially suspended light scattering material (155) that is configured to scatter a predetermined quantum of the admitted light. The suspension body (150) further includes an end cap (156) formed on the second end (152) and comprising a light absorbing material. Light exiting the second end (152) is substantially absorbed by the end cap (156).

19 Claims, 9 Drawing Sheets

STANDARD MEDIA SUSPENSION BODY, OPTICAL PARTICULATE MEASUREMENT INSTRUMENT, AND VERIFICATION METHOD FOR AN OPTICAL PARTICULATE MEASUREMENT INSTRUMENT

CROSS-REFERENCE TO RELATED APPLICATIONS

This is a National Stage entry of International Application No. PCT/US2008/075188, with an international filing date of Sep. 4, 2008, which claims the benefit of U.S. Provisional Application no. 60/971,657, filed Sep. 12, 2007.

BACKGROUND OF THE INVENTION

1. Field of the Invention

The invention is related to the field of optical particulate measurement instruments, and in particular, to a standard media suspension body, an optical particulate measurement instrument, and a verification method for an optical particulate measurement instrument.

2. Statement of the Problem

A turbidimeter or nephelometer is an instrument used for the measure or study of particles in a suspension media. A nephelometer generally refers to an optical instrument for detecting and/or measuring suspended particulates in a liquid or gas colloid. In contrast, a turbidimeter generally refers to an optical instrument for detecting and/or measuring particulate matter in water. Consequently, the suspension media can comprise water. The suspension media is placed in a sample chamber and light is projected through the suspension media as a beam or cone of admitted light into the suspension media. The particles within the suspension scatter the admitted light by a complex interaction of reflection, diffraction, and refraction. A portion of the light scattered from the particles is received by a detector of the instrument.

The detector is typically positioned at about ninety degrees to the incident light source and a resulting axis of illumination. In order to quantify the amount of particles within the suspension media, a comparison must be made of the received scattered light to a scattered light level obtained using a similar suspension media of known particulate concentration. An instrument that is adjusted or calibrated to read the same as the values of the known suspensions can thereafter be used to determine unknown particulate concentrations. The unknown particulate concentrations can be compared to known calibration values and can be determined by estimation or extrapolation from the calibration values.

FIG. 1 shows a prior art turbidimeter/nephelometer. A light source emits light along the axis of illumination and into a suspension contained within a sample chamber. Light from the light source can propagate through the suspension unimpeded and additionally can interact with the suspension by impinging on particles within the suspension. Light impinging on a particle can potentially scatter in one of multiple ray paths, including a backward scatter ray path, a forward scatter ray path, and can scatter along a ray path substantially at ninety degrees to the incident beam. Light scattered at a right angle impinges on and is quantified by a light receiver. The light receiver converts photon energy into an electrical signal by means of a photoelectric effect. The electrical signal, usually weak or low in signal strength, can be amplified and processed in order to determine a particulate concentration. The particulate concentration can subsequently be output to a meter, display, printout, or other useful indicator.

In order to reduce the cost of unnecessary calibrations, various reusable verification methods and devices have been devised to check the readiness and fitness of use of a turbidimeter or nephelometer. Verification is usually performed after a calibration procedure, wherein verification information is obtained and stored for future verification use. The stored verification information is subsequently compared to instrument readings in the field, whereupon a determination is made as to the need for service by comparing an instrument reading to the stored verification information. Periodic verification is especially critical in applications such as pharmaceuticals manufacturing, food and beverage production, or the production and distribution of potable water.

Current agency regulatory requirements for potable water, such as regulations promulgated by the Environmental Protection Agency (EPA), are drafted to compel and control testing of turbidity. This testing is performed in order to insure the amount of particulate material, pathogens, or parasites in a water distribution system are below a predetermined value or threshold. Commonly, the regulatory requirements dictate that particulates not exceed about one Nephelometric Turbidity Unit (NTU), which greatly reduces the heath risk to the general population. Therefore, periodic testing of the accuracy of turbidity measurement equipment must be conducted, where the turbidity measurement equipment is used to determine the quality of the water. Testing is performed under guidelines set by country, government, and/or state and local municipalities to insure the accuracy of the reported values of turbidity.

Existing methods to validate the compliance of a turbidity system can make use of primary liquid standards, such as suspensions of Formazin and/or liquid suspensions of styrene divinyl benzene polymer beads (SDB or $BaS_4$). Alternatively, compliance testing can use secondary liquid standards such as liquid Latex or solid secondary standards such as acrylics, glass, or glass-ceramics such as SCHOTT 'Zerodur' which has an equivalent value as compared to the primary standard. Confidence in the security of drinking water distribution networks is related to the frequency of the validation of the operational readiness and accuracy of the nephelometric measurement systems.

A primary standard can be used for verification, as in U.S. Pat. No. 7,180,594, to Williams. However, usage of such primary standards is expensive, and therefore primary standards are undesirable for frequent or widespread verification.

Alternatively, solid standards have been used in place of liquid standards, as disclosed in U.S. Pat. No. 5,912,737 to Bannerjee or as disclosed in U.S. Pat. No. 5,059,811 to King. However, this prior art approach also has drawbacks. A solid turbidity standard must be precisely aligned and oriented in relationship to both the illuminating beam and the detection means. In addition, the use of solid standards requires service of the operation nephelometric system involving complete removal of the liquid sample and cleaning of all surfaces.

Prior art verification devices and methods generally require that the instrument sample compartment be cleaned and dried before installation of the verification device. Other prior art verification devices and methods require replacement of the sample chamber with a chamber or cell containing a fixed value of turbidity to compare against the last recorded verification.

Consequently, there is a need to empty and clean the test chamber of the turbidity or nephelometry meter, as the test chamber has to be serviced and conditioned before either a liquid test fluid or a solid test master can be used for a verification process. Though cleaning is not required on a nephelometric apparatus that has never been in service, per U.S. Pat. No. 5,757,481 to O'Brien, it does pose considerable effort to routinely bring a field-operational nephelometric system to a condition of clean and dry. Failure to completely remove the sample can result in the formation of a condensate of the sample on a solid standard.

Calibration by use of standard suspension concentrations placed within an empty, dry sample chamber is time consuming and expensive. A new standard suspension is required for each use in order to assure the correct value of the standard and to lessen or minimize the contamination of the standard that can occur if the standard is reused. In addition, prior to calibration, the cleanliness of the instrument must be assured before introduction of the standard into the sample chamber so as not to dilute or alter the results by contamination of the standard suspension. Upon completion of verification, the instrument must again be serviced in order to restore the instrument to an operational condition. The process of restoration or removal of the verification device and can alter or negate the integrity of the instrument readiness or ability to read accurately by improperly performed assembly or restoration.

Failure to align and orient a solid standard precisely or failure to bring the nephelometric system to a state of being properly clean and dry affects the precision of the measurement. This can in turn lead to unnecessary calibration, loss of productivity, or failure to detect a nephelometric system that is out of tolerance or unfit for use. Operation after an improper or incomplete calibration or verification can consequently pose a threat to the integrity of portable water distribution.

Aspects Of The Invention

In some aspects of the invention, a standard media suspension body for verification of an optical particulate measurement instrument and configured to be at least partially immersed in a sample fluid comprises:

a substantially solid three-dimensional outer surface including a first end and a second end disposed along an axis of illumination A and at least one outer surface extending between the first end and the second end, with the first end being configured to admit light into the standard media suspension body;

an inner volume, with at least a portion of the inner volume including a substantially suspended light scattering material that is configured to scatter a predetermined quantum of the admitted light; and an end cap formed on the second end and comprising a light absorbing material, wherein light exiting the second end is substantially absorbed by the end cap.

Preferably, the standard media suspension body includes a refractive index that substantially matches a sample fluid refractive index.

Preferably, the standard media suspension body further comprises a substantially solid body of suspension material and light scattering material held in suspension by the solid suspension material.

Preferably, the standard media suspension body further comprises a substantially solid body of suspension material and amorphous and non-amorphous molecular bonds in at least a portion of the suspension material.

Preferably, the standard media suspension body further comprises a substantially solid body of suspension material and bubbles distributed through at least a portion of the suspension material.

Preferably, the standard media suspension body further comprises an outer shell and a suspension material held in the outer shell, with the suspension material including the suspended light scattering material.

Preferably, the suspension material comprises a suspension liquid, a suspension gel, a semisolid, or other settable liquid contained within the outer shell.

Preferably, the standard media suspension body further comprises a first optical surface at the first end of the standard media suspension body for admitting the impinging light entering the standard media suspension body, a third optical surface at the second end for the transmittance of unscattered light propagating substantially through and exiting the standard media suspension body substantially along the axis of illumination A, and a second optical surface extending at least partially between the first end and the second end for the transmittance of scattered light exiting from the standard media suspension body substantially perpendicularly to the axis of illumination A, with the first end polished to form the first optical surface, the second end polished to form the third optical surface, with the first end and the second end disposed along the axis of illumination A, and at least a portion of an outer surface between the first end and the second end being polished to form the second optical surface.

In some aspects of the invention, an optical particulate measurement instrument comprises:

a light source positioned to emit light into a test chamber along an axis of illumination A;

a light receiver positioned at least partially in the test chamber and positioned to receive light along a light scattering path;

a substantially open sample chamber positioned at a juncture of the axis of illumination A and the light scattering path, with the sample chamber configured to hold a sample fluid for measurement; and a standard media suspension body at least partially immersed in the sample fluid in the sample chamber, with the standard media suspension body being removable and being configured to scatter a predetermined quantum of the admitted light;

wherein the optical particulate measurement instrument is configured to emit the light into the standard media suspension body, receive the scattered light that is scattered by the standard media suspension body and that has passed through at least some of the sample fluid, and perform a verification of the optical particulate measurement instrument using the scattered light.

Preferably, the optical particulate measurement instrument is configured to emit light into the standard media suspension body, receive scattered light that is scattered by the standard media suspension body and that has passed through at least some of the sample fluid, determine a particulate concentration value using the received scattered light, determine a difference between the particulate concentration value and a reference value, compare the difference to a predetermined tolerance range, generate a verification success indication if the difference is within the predetermined tolerance range, and generate a verification failure indication if the difference is outside the predetermined tolerance range.

Preferably, the optical particulate measurement instrument is further configured to emit light into the standard media suspension body, receive the scattered light, determine a particulate concentration value using the received scattered light, emit light into the sample fluid in the sample chamber without the standard media suspension body, generate a second concentration value without the standard media suspension body, determine a difference between the particulate concentration value and the second concentration value, compare the difference to a predetermined tolerance range, generate a verification success indication if the difference is within the predetermined tolerance range, and generate a verification failure indication if the difference is outside the predetermined tolerance range.

Preferably, the standard media suspension body comprises a substantially solid three-dimensional outer surface including a first end and a second end disposed along an axis of illumination A and at least one outer surface extending between the first end and the second end, with the first end being configured to admit the impinging light, and an inner volume, with at least a portion of the inner volume including a substantially suspended light scattering material that is configured to scatter a predetermined quantum of the admitted light received from a light source out of the at least one outer surface.

Preferably, the standard media suspension body comprises a substantially solid three-dimensional outer surface including a first end and a second end disposed along an axis of illumination A and at least one outer surface extending between the first end and the second end, with the first end being configured to admit the impinging light, an inner volume, with at least a portion of the inner volume including a substantially suspended light scattering material that is configured to scatter a predetermined quantum of the admitted light received from a light source out of the at least one outer surface, and an end cap formed on the second end and comprising a light absorbing material, wherein light exiting the second end is substantially absorbed by the end cap.

Preferably, a suspension body refractive index is selected to substantially match a sample fluid refractive index.

Preferably, the standard media suspension body further comprises a substantially solid body of suspension material, and light scattering material held in suspension by the solid suspension material.

Preferably, the standard media suspension body further comprises a substantially solid body of suspension material and amorphous and non-amorphous molecular bonds in at least a portion of the suspension material.

Preferably, the standard media suspension body further comprises a substantially solid body of suspension material and bubbles distributed through at least a portion of the suspension material.

Preferably, the standard media suspension body further comprises an outer shell and a suspension material held in the outer shell, with the suspension material including the suspended light scattering material.

Preferably, the suspension material comprising a suspension liquid, a suspension gel, a semisolid, or other settable liquid contained within the outer shell.

Preferably, the standard media suspension body further comprises a first optical surface at a first end of the standard media suspension body for admitting the impinging light entering the standard media suspension body, a third optical surface at a second end for the transmittance of unscattered light propagating substantially through and exiting the standard media suspension body substantially along the axis of illumination A, and a second optical surface extending at least partially between the first end and the second end for the transmittance of the scattered light exiting from the standard media suspension body substantially perpendicularly to the axis of illumination A, with a first end polished to form the first optical surface, a second end polished to form the third optical surface, with the first end and the second end disposed along the axis of illumination A, and at least a portion of an outer surface between the first end and the second end being polished to form the second optical surface.

A verification method for an optical particulate measurement instrument comprises:

emitting light into a removable standard media suspension body at least partially immersed in a sample fluid held in a substantially open sample chamber of the optical particulate measurement instrument, with the standard media suspension body being configured to scatter a predetermined quantum of the admitted light;

receiving scattered light that is scattered by the standard media suspension body and that has passed through at least some of the sample fluid; and performing a verification of the optical particulate measurement instrument using the scattered light.

Preferably, the standard media suspension body is three-dimensional.

Preferably, the standard media suspension body is substantially fully immersed in the sample fluid.

Preferably, the standard media suspension body includes a refractive index that substantially matches a sample fluid refractive index.

Preferably, performing the verification further comprises determining a particulate concentration value using the received scattered light, determining a difference between the particulate concentration value and a reference value, comparing the difference to a predetermined tolerance range, and generating a verification success indication if the difference is within the predetermined tolerance range.

Preferably, further comprising generating a verification failure indication if the difference is outside the predetermined tolerance range.

A verification method for an optical particulate measurement instrument comprises:

emitting light into a removable standard media suspension body at least partially immersed in a sample fluid held in a substantially open sample chamber of the optical particulate measurement instrument, with the standard media suspension body being configured to scatter a predetermined quantum of the admitted light;

receiving scattered light that is scattered by the standard media suspension body and that has passed through at least some of the sample fluid;

determining a particulate concentration value using the received scattered light;

determining a difference between the particulate concentration value and a reference value;

comparing the difference to a predetermined tolerance range; and generating a verification success indication if the difference is within the predetermined tolerance range.

Preferably, the standard media suspension body is three-dimensional.

Preferably, the standard media suspension body is substantially fully immersed in the sample fluid.

Preferably, the standard media suspension body includes a refractive index that substantially matches a sample fluid refractive index.

Preferably, the method further comprises generating a verification failure indication if the difference is outside the predetermined tolerance range.

A verification method for an optical particulate measurement instrument comprises:

emitting light into a standard media suspension body at least partially immersed in a sample fluid held in a sample chamber of the optical particulate measurement instrument, with the standard media suspension body being configured to scatter a predetermined quantum of the admitted light;

receiving scattered light that is scattered by the standard media suspension body and that has passed through at least some of the sample fluid;

determining a particulate concentration value using the received scattered light;

emitting light into the sample fluid in the sample chamber without the standard media suspension body;

generating a second concentration value without the standard media suspension body;

determining a difference between the particulate concentration value and the second concentration value;

comparing the difference to a predetermined tolerance range; and generating a verification success indication if the difference is within the predetermined tolerance range.

Preferably, the method further comprises generating a verification failure indication if the difference is outside the predetermined tolerance range.

Preferably, the standard media suspension body is three-dimensional.

Preferably, the standard media suspension body is substantially fully immersed in the sample fluid.

Preferably, the standard media suspension body includes a refractive index that substantially matches a sample fluid refractive index.

A verification method for an optical particulate measurement instrument comprises:

emitting light into a first standard media suspension body at least partially immersed in a sample fluid held in a sample chamber of the optical particulate measurement instrument, with the standard media suspension body being configured to scatter a predetermined quantum of the first admitted light;

determining a first particulate concentration value using first scattered light that is scattered by the first standard media suspension body and that has passed through at least some of the sample fluid;

emitting light into a second standard media suspension body at least partially immersed in the sample fluid and likewise configured to scatter the predetermined quantum of the second admitted light, wherein the second standard media suspension body includes an end cap formed on a second end and wherein the second light exiting the second end is substantially absorbed by the end cap;

determining a second concentration value using second scattered light that is scattered by the second standard media suspension body and that has passed through at least some of the sample fluid;

determining a difference between the first particulate concentration value and the second particulate concentration value, wherein the difference is related to light scattered by the sample chamber.

Preferably, the method further comprises generating a verification failure indication if the difference exceeds a predetermined chamber scattering threshold.

Preferably, the standard media suspension body is three-dimensional.

Preferably, the standard media suspension body is substantially fully immersed in the sample fluid.

Preferably, the standard media suspension body includes a refractive index that substantially matches a sample fluid refractive index.

DESCRIPTION OF THE DRAWINGS

The same reference number represents the same element on all drawings. It should be understood that the drawings are not necessarily to scale.

DETAILED DESCRIPTION OF THE INVENTION

FIGS. 2-11 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
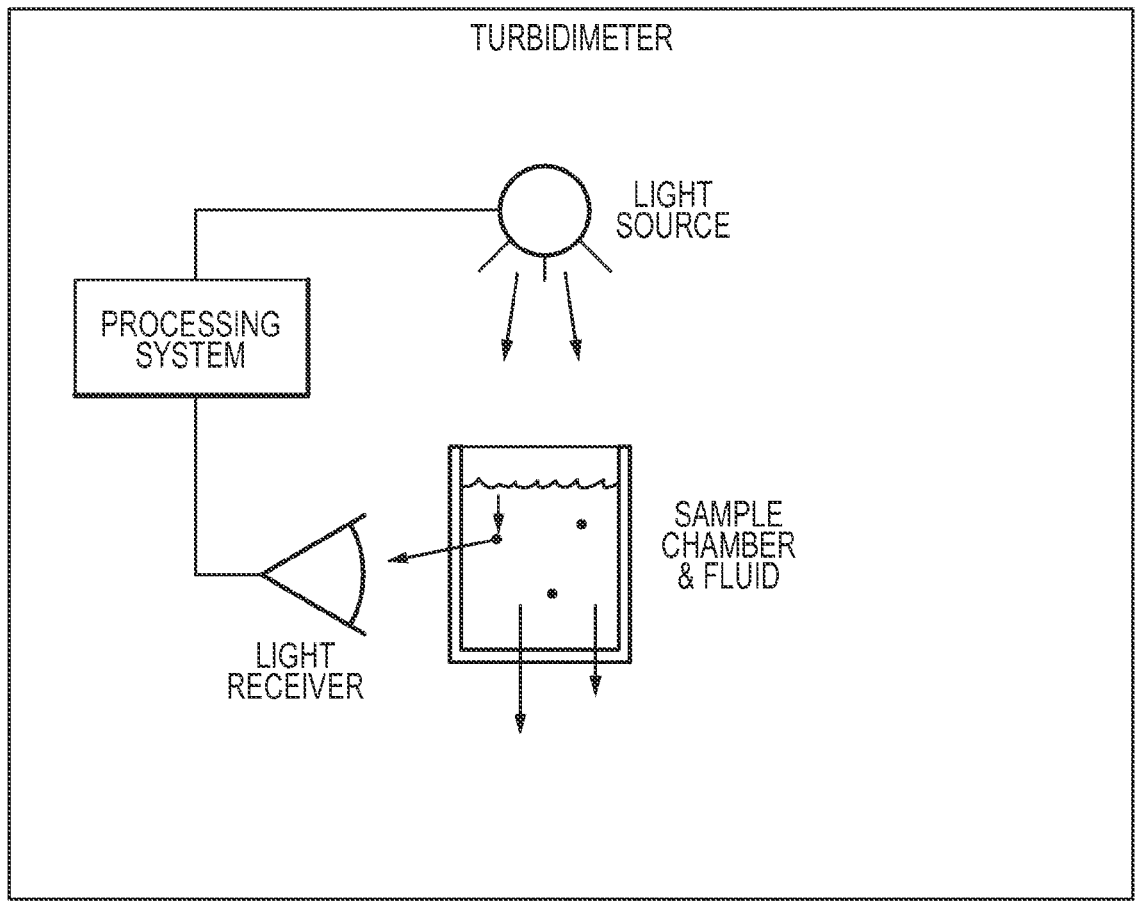
FIG. 1 shows a prior art turbidimeter/nephelometer.
Figure 2:
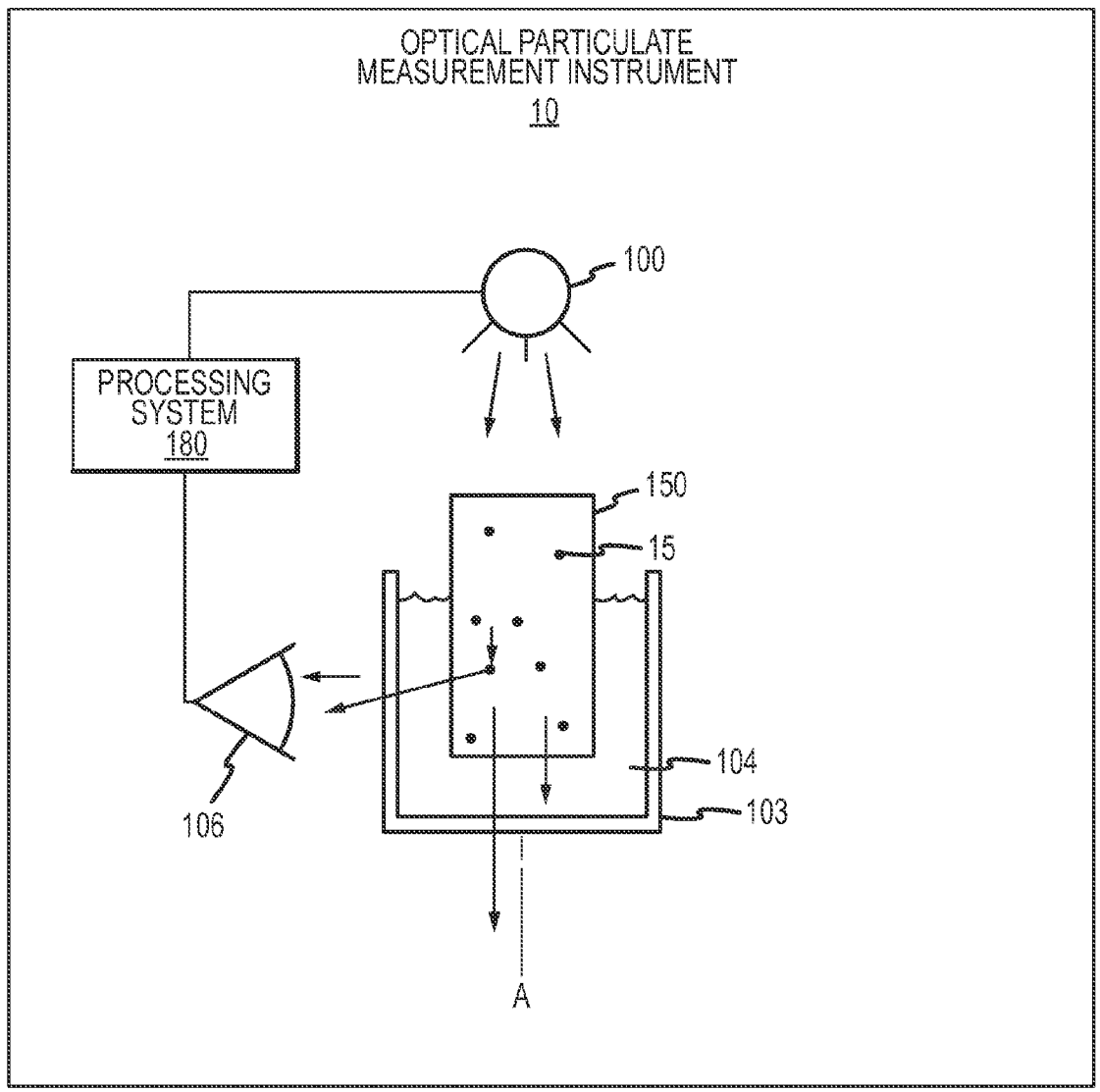
FIG. 2 shows an optical particulate measurement instrument according to an embodiment of the invention.

FIG. 2 shows an optical particulate measurement instrument 10 according to an embodiment of the invention. The optical particulate measurement instrument 10 includes a light source 100, a test chamber 103, a light receiver 106, and a processing system 180. The test chamber 103 is configured to hold a quantity of a sample fluid 104. The optical particulate measurement instrument 10 is configured to measure a particulate concentration in the sample fluid 104.

A standard media suspension body 150 is configured to fit at least partially into the sample chamber 103 and is configured to be at least partially immersed in the sample fluid 104. In some embodiments, the suspension body 150 is configured to fit completely into the sample chamber 103. In some embodiments, the suspension body 150 is configured to be substantially fully immersed in the sample fluid 104.

The standard media suspension body 150 is configured for verification of an optical particulate measurement instrument and configured to be at least partially immersed in a sample fluid. The suspension body 150 comprises a substantially solid three-dimensional outer surface including a first end 151 and a second end 152 disposed along an axis of illumination A and at least one outer surface 153 extending between the first end 151 and the second end 152 (see FIG. 3 and the accompanying discussion). The first end 151 is configured to admit impinging light. The suspension body 150 further comprises an inner volume, with at least a portion of the inner volume including a substantially suspended light scattering material 155 that is configured to scatter a predetermined quantum of the admitted light. The suspension body 150 in some embodiments further comprises an end cap 156 formed on the second end and comprising a light absorbing material, wherein light exiting the second end 152 is substantially absorbed by the end cap 156.

Light is scattered by particles suspended and distributed within the suspension body 150, i.e., by the light scattering material 155. The suspension body 150 can therefore result in unscattered first light that propagates through the suspension body 150 and that is unaffected by the light scattering material and scattered first light that is scattered away from the first light path by the light scattering material within the suspension body 150. At least some of the scattered first light can be detected and received by the light receiver 106. Measurement of the scattered first light received by the light receiver 106 can be used to perform a verification process for the optical particulate measurement instrument 10.

The light scatter occurs as result of the standard body 150 and not due to sample fluid 104 still present in the instrument 10. It should be understood that the sample fluid 104 will have a negligible effect on the verification process even though the scattered light may pass through an appreciable amount or distance of the sample fluid 104. Any obscuration, absorbance, or secondary scatter due to particulate matter in the sample fluid 104, even at the maximum permissible values of turbidity in potable water, will not have an appreciable effect on the precision of the verification process. The effect will typically be less than about 0.0002 NTU, permitting verification of the instrument 10 to predetermined performance specifications and operational readiness in the environment of use. This is a simple, fast, and economical method that more closely emulates actual use than traditional verification processes.

The standard media suspension body 150 can comprise a removable component and can be inserted into and removed from the sample chamber 103. However, the standard media suspension body 150 is configured to be substantially immobile when inserted into the sample chamber 103. The standard media suspension body 150 can be inserted into the sample chamber 103 when the sample chamber 103 is empty and/or dry. To this end, the sample chamber 103 can be substantially open, such as having an open or partially open top, for example. The light source 100 and the light receiver 106 do not need to be removed from the optical particulate measurement instrument 10 in order for a verification/calibration operation to be performed.

The standard media suspension body 150 comprises a simple and effective way for an operator, including an untrained operator, to perform a verification process. The standard media suspension body 150 can be inserted into and removed from the sample chamber 103. Therefore, the standard media suspension body 150 can be used as needed. The standard media suspension body 150 is operator cleanable. The standard media suspension body 150 can be used as a transfer standard, wherein the standard media suspension body 150 can be sent to a laboratory for independent nephelometric verification not dependent on the measurement instrument 10.

The standard media suspension body 150 can be inserted into the sample chamber 103 when the sample chamber 103 contains a volume of the sample fluid 104, as shown. The standard media suspension body 150 can displace at least some of the sample fluid 104. The optical particulate measurement instrument 10 can perform a self-calibration or self-verification procedure using the standard media suspension body 150.

The sample fluid 104 can be substantially immobile and non-flowing in the sample chamber 103. Alternatively, the sample fluid 104 can be moving through the sample chamber 103. If moving or flowing, the sample fluid 104 can comprise either turbulent or laminar flow.

The standard media suspension body 150 in some embodiments is substantially non-soluble, such as where the entire standard media suspension body 150 comprises a suspension material. Alternatively, where the standard media suspension body 150 includes an outer shell, the suspension material can be at least partially soluble.

The standard media suspension body 150 in some embodiments possesses a refractive index that substantially matches a sample fluid refractive index. Consequently, the refractive index similarity substantially eliminates reflection and refraction of light from an interface of an external surface of the standard media suspension body 150 and the sample fluid 104.

The light source 100 emits light along the axis of illumination A (vertical arrows). The light receiver 106 is positioned to receive scattered light traveling substantially along a light scattering path (horizontal and nearly horizontal arrows). The sample chamber 103 is positioned substantially at a juncture of the axis of illumination A and the light scattering path leading into the light receiver 106. Consequently, light emitted by the light source 100 is directed through the sample fluid 104. When the suspension body 150 is not in place in the sample chamber 103, then light scattered by the sample fluid 104 will be received by the light receiver 106.

The test chamber 103 typically holds the sample fluid 104 for measurement. The sample fluid 104 can include particles, such as suspended particles, for example (not shown in this figure for clarity). The test chamber 103 can be substantially aligned and centered along the axis of illumination A. The test chamber 103 is at least partially constructed of a light transmissive material. Consequently, unscattered first light from the light source 100 may be allowed to pass through the test chamber 103. In addition, scattered first light that is scattered by particles in the sample fluid can pass out of the test chamber 103 at various angles, such as along the light scattering path.

The processing system 180 is connected to the light receiver 106 and to the light source 100. The processing system 180 can further be connected to any manner of user interface (not shown), including user input and/or output devices. The processing system 180 can operate the light source 100 and can receive a light measurement from the light receiver 106 and determine a particulate concentration in the sample fluid 104.

The processing system 180 can store various values, including one or more verification values. The one or more verification values can include factory-stored verification reference values, such as reference values obtained through a calibration process. Alternatively, the one or more verification values can comprise previous measurement and/or verification values that have been stored for subsequent verification processes, such as historical reference values.

The light receiver 106 is positioned out of and away from the axis of illumination A of the light source 100. In some embodiments, the light receiver 106 is substantially at a right angle from the axis of illumination A. Alternatively, the light receiver 106 can be positioned obliquely from the axis of illumination A. Consequently, the light receiver 106 is positioned to receive scattered first light from the test chamber 103. In some embodiments, the light receiver 106 is positioned to receive light that is scattered at an angle of about ninety degrees from the axis of illumination A of the light source 100.

The light source 100 comprises a measurement light source for performing an optical measurement. The light source 100 is positioned to emit first light into the test chamber 103. The first light can be substantially collimated, focused, or otherwise directed toward the test chamber 103. Consequently, it should be understood that the optical particulate measurement instrument 10 can include any manner of optical devices positioned between the various optical components. For example, the optical devices can include lenses, filters, apertures, collimators, and reflectors. However, other optical devices are also contemplated and are within the scope of the description and claims.

Light is scattered by particles in the sample fluid in the test chamber 103 during measurement of the sample fluid 104. The test chamber 103 can therefore result in unscattered first light that propagates through the test chamber 103 and that is unaffected by the sample fluid 104 and scattered first light that is scattered away from the first light path by particles in the test chamber 103. At least some of the scattered first light can be detected and received by the light receiver 106. Measurement of the scattered first light received by the light receiver 106 can be used to determine an amount of particulate in the sample fluid.

The processing system 180 is connected to the light receiver 106 and receives an electrical measurement signal therefrom during normal operation. The measurement signal is proportional to the scattered light that is received from the sample chamber 103. The processing system 180 processes the measurement signal to generate a sample measurement value. In some embodiments, the sample measurement value comprises a measure of particles in the sample fluid.

The processing system 180 in some embodiments receives user inputs and conducts a measurement. This includes turning on and off the light source 100, receiving a measurement signal from the light receiver 106, and calculating a particulate concentration value from the measurement signal. The processing system 180 can further output the particulate concentration value, such as by generating a display, an output, or printout, for example. In addition, the particulate concentration value can be stored for later comparisons or trend analyses.

Figure 3:
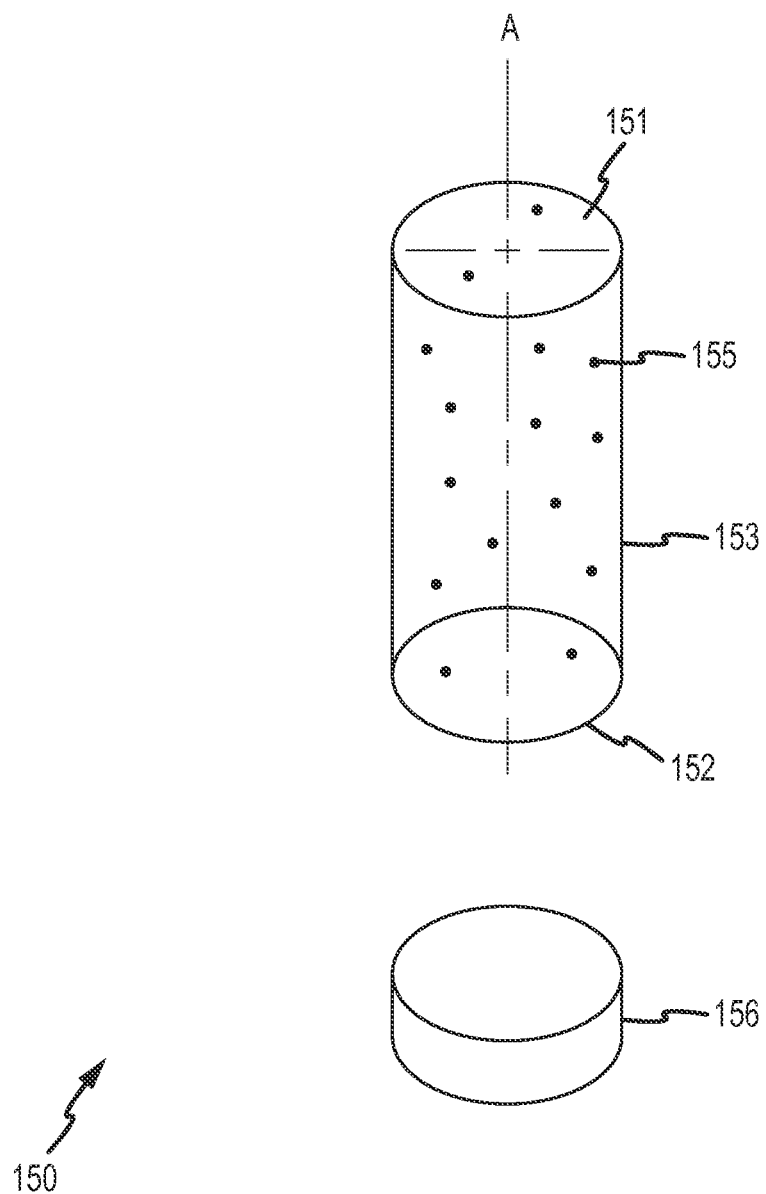
FIG. 3 shows detail of a standard media suspension body according to an embodiment of the invention.

FIG. 3 shows detail of the standard media suspension body 150 according to an embodiment of the invention. Components in common with other figures share common reference numbers. The suspension body 150 is three-dimensional and includes the substantially solid outer surface including the first end 151, the second end 152, and the at least one outer surface 153 extending between the first end 151 and the second end 152. The first end 151 and the second end 152 are positioned along an axis of illumination A. The suspension body 150 further includes the inner volume, with at least a portion of the inner volume including the substantially suspended light scattering material 155 that is configured to scatter a predetermined quantum of the admitted light impingent upon the suspension body 150 along the axis of illumination A.

The suspension body 150 can be chosen to have a refractive index that substantially matches a sample fluid refractive index. Consequently, light passing from the sample fluid 104 into the suspension body 150 will be minimally refracted and will not substantially change in direction upon entry. Likewise, scattered light exiting the suspension body 150 will not change in direction.

The first end 151 can comprise a first optical surface. Light from a light source can enter the first end 151. The second end 152 can comprise a second optical surface. The first optical surface and the third optical surface in some embodiments are substantially perpendicular to the axis of illumination A. In some embodiments, the second optical surface is substantially parallel to the axis of illumination A. In some embodiments, light that substantially propagates through the suspension body 150 can exit from the second end 152. The at least one outer surface 153 comprises a third optical surface. The optical surfaces can comprise polished surfaces, for example. The third optical surface can comprise at least a portion of the at least one outer surface 153. The at least one outer surface 153/third optical surface includes at least one transparent surface or region that is located approximately ninety degrees from the first end 151 and the axis of illumination A. Light scattered within the suspension body 150 can exit through the at least one outer surface 153/third optical surface, for example.

The at least one outer surface 153/third optical surface can comprise a single surface, such as the suspension body 150 having a circular or ovoid cross-sectional shape, for example. Alternatively, the at least one outer surface 153/third optical surface can comprise multiple surfaces, such as rectangular, square, hexagonal in cross-section, for example. Other cross-sectional shapes are contemplated and are within the scope of the description and claims.

The suspension body 150 in some embodiments includes a light absorbing end cap 156. The end cap 156 in this embodiment absorbs the light that propagates through the suspension body 150 without scattering. The light absorbing end cap 156 therefore prevents this unscattered light from internally reflecting within the optical particulate measurement instrument 10 and possibly impinging on the light detector 106.

The standard media suspension body 150 can be formed in various ways and can comprise various components. In some embodiments, the standard media suspension body 150 comprises a substantially solid body of suspension material and light scattering material held in suspension by the solid suspension material. The light scattering material can be cast into or otherwise formed or deposited in the solid body. In some embodiments, the standard media suspension body 150 comprises a substantially solid body of suspension material and amorphous and non-amorphous molecular bonds in at least a portion of the suspension material. In some embodiments, the standard media suspension body 150 comprises a substantially solid body of suspension material and bubbles distributed through at least a portion of the suspension material. In some embodiments, the standard media suspension body 150 comprises an outer shell and a suspension material held in the outer shell, with the suspension material including the suspended light scattering material. In some embodiments, the suspension material comprises a suspension liquid, a suspension gel, a semisolid, or other settable liquid contained within the outer shell.

The second end 152 is designed to be completely immersed in the sample fluid 104. At least a portion of the at least one outer surface 153 can also be immersed. The first end 151 can also be designed to be completely immersed in the sample fluid 104. When the first end 151 is at least slightly immersed, the first end 151 can advantageously form a surface of illumination, transporting impinging light to the suspension body 150 and eliminating the need for strict alignment of the suspension body 150 (see FIGS. 4-5 and the accompanying discussion).

The suspension body 150 is optically coupled to the sample fluid 103 by the immersion. Reflection loss, refraction, and surface imperfections on the surface of the suspension body 150 and the effects on measurement precision are largely mitigated by a similarity of refractive indices between the sample fluid 104 and the suspension body 150. Advantageously, the light detector 106 is not subjected to changes in environment during verification, which eliminates temperature effects caused by removal of the sample fluid 104. In addition, the suspension body 150 does not adversely change an area of view of the light detector 106 (such as due to refractive index changes) as is the case when the sample fluid 104 is removed in the prior art.

Another advantage is presented by the light absorbing end cap 156. The light absorbing end cap 156 prevents light propagating through the suspension body 150 from being internally reflected and subsequently managing to impinge on the light detector 106.

Advantageously, the suspension body 150 can be used with and without the light absorbing end cap 156. The suspension body 150 without the light absorbing end cap 156 can be used to measure a signal contribution due to light scatter within the instrument 10. The suspension body 150 can further be used with the light absorbing end cap 156 in order to generate a difference in readings of the instrument 10 or as a measure of the total signal due to the suspension body 150 plus the contribution in signal caused by internal reflection and/or scatter. The utility of the total or difference measurement provides a means for determining a need for service or reconditioning of the optical particulate measurement instrument 10.

Figure 4:
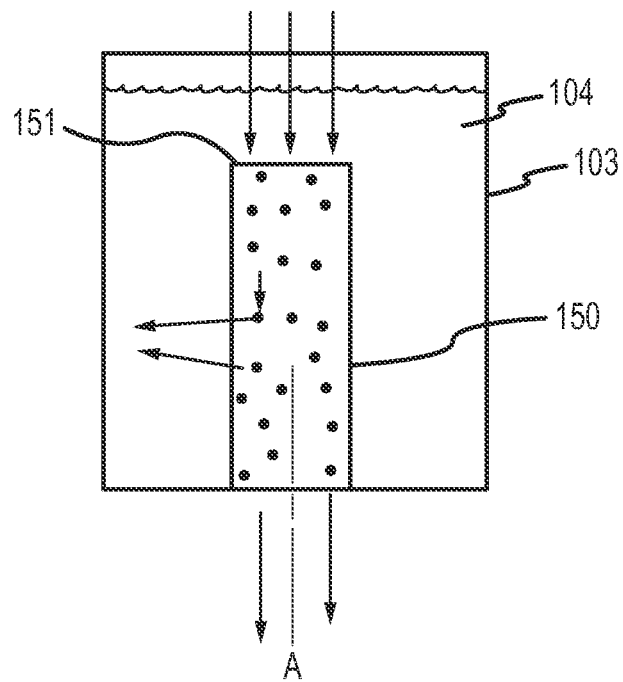
FIG. 4 shows a typical immersion of the standard media suspension body in a sample chamber including a sample fluid.

FIG. 4 shows a typical immersion of the standard media suspension body 150 in a sample chamber 103 including a sample fluid 104. The suspension body 150 is positioned so that the axis of illumination A is substantially vertical. The suspension body 150 can optionally include the light absorbing end cap 156 (not shown for simplicity).

The suspension body 150 can be partially or fully immersed, as previously discussed. The first end 151 can be fully immersed, as shown, or can be kept up out of the sample fluid 104.

The suspension body 150 in some embodiments can be placed or held in the sample chamber 103 by any manner of guide(s), holder(s), or mechanism(s). Alternatively, the suspension body 150 can possess a specific gravity that enables the suspension body 150 to stay in position in the sample fluid 104. Alternatively, in some embodiments, the suspension body 150 can rest on the bottom of the sample chamber 103, as shown.

Figure 5:
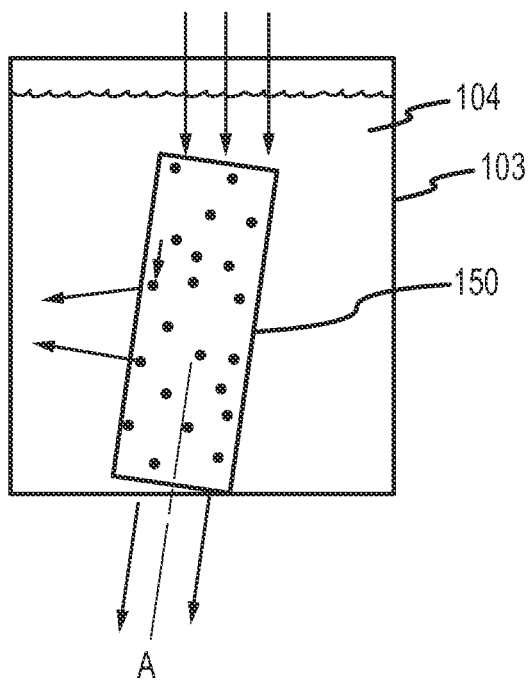
FIG. 5 shows the suspension body positioned in the sample chamber in a less than optimal manner.

FIG. 5 shows the suspension body 150 positioned in the sample chamber 103 in a less than optimal manner. The suspension body 150 is positioned so that the axis of illumination A deviates from the vertical. However, the angle of incidence to the sample liquid remains at about ninety degrees. As a result, where the deviation is not excessive, the impinging light (upper arrows) can still enter and travel substantially through the suspension body 150. Scattered light can still exit from the suspension body 150 and travel toward the light detector 106.

Light emitted into a cylindrical side surface of a prior art cylindrical body in a turbidimeter can cause light refraction. One such body is shown in U.S. Pat. No. 4,367,187 to Beers. Admitted light beam distortion will occur if there is a significant difference between the material of the prior art cylindrical body and the sample fluid. The distortion can lead to errors in calibration. In the prior art, this can limit the type of material that can be used for calibration or zeroing purposes.

In contrast, in the standard media suspension body 150 according to the invention, the admitted light beam is largely unaffected by the refractive index of the sample fluid because the impinging beam is introduced along the axis of the standard media suspension body 150 where little or no refraction occurs at the planar optical surface.

Figure 6:
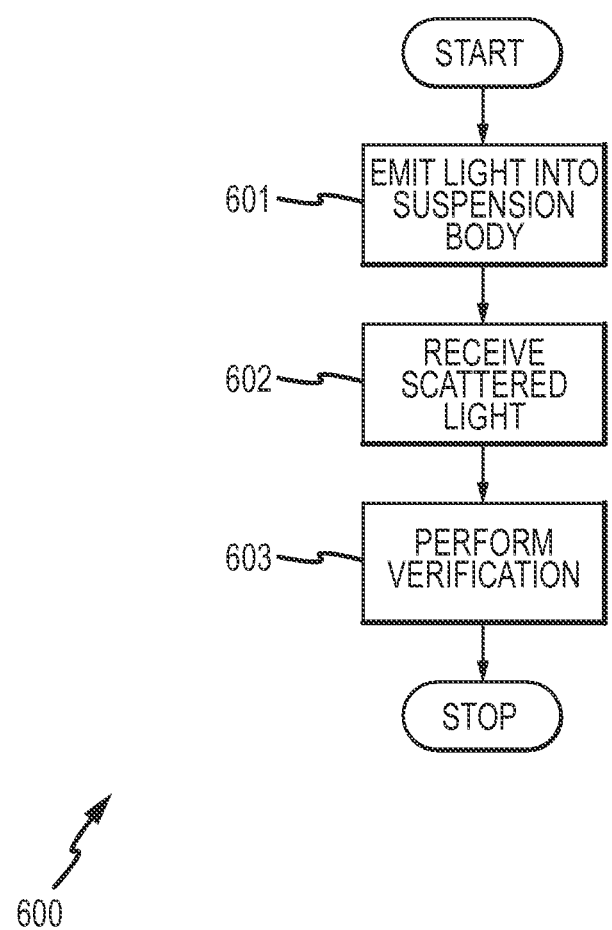
FIG. 6 is a flowchart of a verification method for an optical particulate measurement instrument according to an embodiment of the invention.

FIG. 6 is a flowchart 600 of a verification method for an optical particulate measurement instrument according to an embodiment of the invention. In step 601, light is emitted into a sample chamber and into a standard media suspension body. The suspension body is at least partially immersed in a sample fluid. The suspension body in some embodiments can be substantially fully immersed.

In step 602, a light detector receives scattered light that is scattered within the suspension body. The suspension body can be designed to scatter a predetermined quantum of the admitted light. For example, the suspension body can be designed to substantially match a turbidity standard suspension in some embodiments. However, the suspension body can alternatively include other light scattering levels.

In step 603, a verification process is performed using the scattered light. The verification process can provide a determination as to whether the optical particulate measurement instrument 10 is working properly or whether the optical particulate measurement instrument 10 needs additional cleaning, calibration, or repair or refurbishment.

Figure 7:
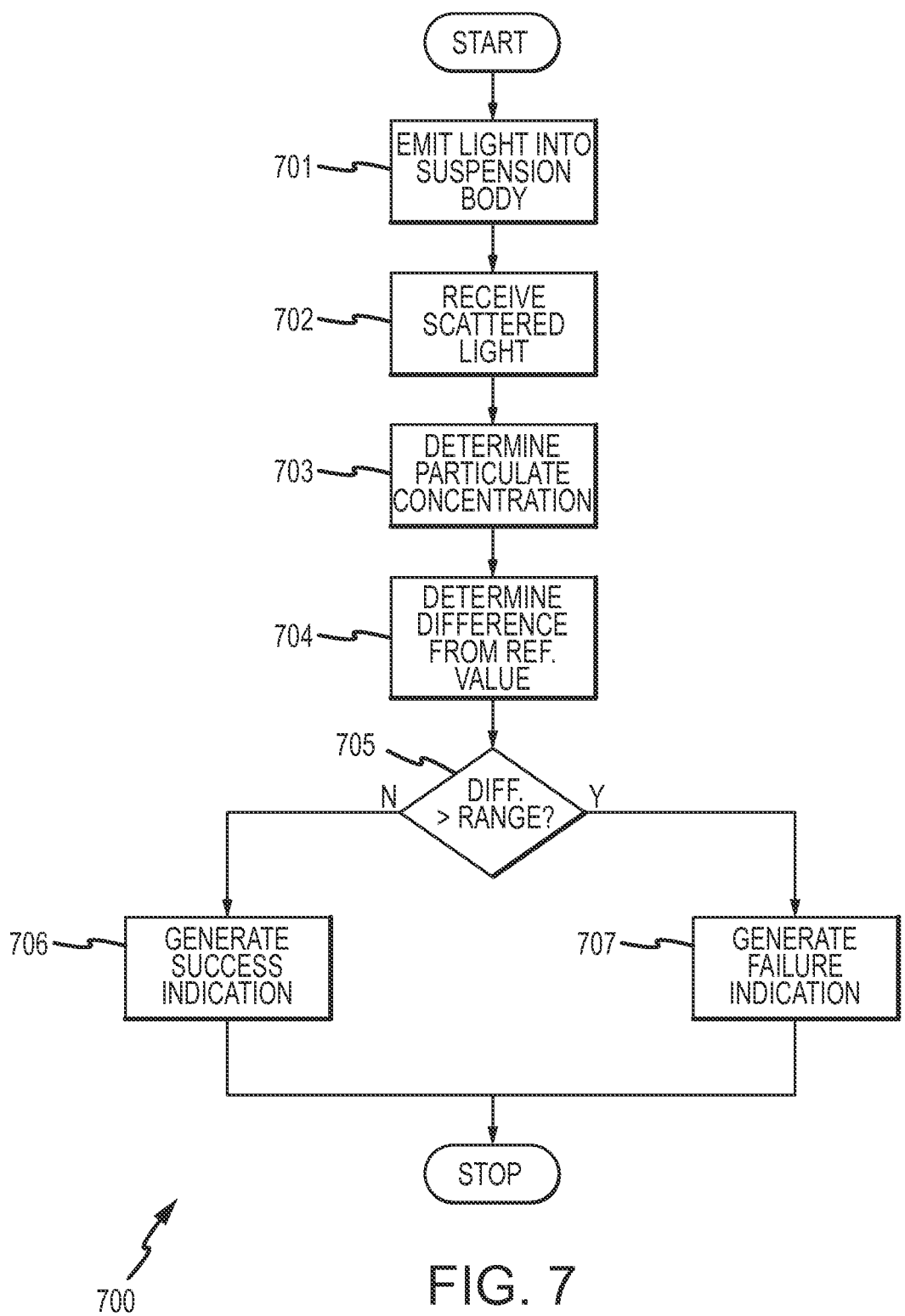
FIG. 7 is a flowchart of a verification method for an optical particulate measurement instrument according to an embodiment of the invention.

FIG. 7 is a flowchart 700 of a verification method for an optical particulate measurement instrument according to an embodiment of the invention. In step 701, light is emitted into a sample chamber and into a standard media suspension body, as previously discussed.

In step 702, a light detector receives scattered light that is scattered within the suspension body, as previously discussed.

In step 703, a particulate concentration value is determined from the received scattered light. The particulate concentration value can be generated in a known manner from an intensity of the received scattered light. The particulate concentration value can be expressed in known units, such as in Nephelometric Turbidity Units (NTUs), for example.

In step 704, a difference between the particulate concentration value and a reference value is determined. The reference value can comprise a stored value, for example. The reference value can comprise a historical value, for example. The reference value can comprise a previous measurement, such as a verification measurement (i.e., a particulate concentration value) taken after a factory calibration procedure or after a cleaning, repair, or refurbishment operation.

In step 705, the difference is compared to a predetermined acceptable range. If the difference is not greater than the predetermined acceptable range, then the method proceeds to step 706. If the difference is greater than the predetermined acceptable range, then the method proceeds to step 707.

In step 706, a success indication is generated. The success indication indicates that the difference was within the predetermined acceptable range and the optical measurement instrument has passed the verification process. Consequently, the success indication further indicates that the optical measurement instrument can continue to be used. The method exits.

In step 707, a failure indication is generated. The failure indication indicates that the difference exceeded the predetermined acceptable range and the optical measurement instrument failed the verification process. Consequently, the failure indication further indicates that some manner of calibration, cleaning, or refurbishment or repair of the instrument is needed or required. The method exits.

Figure 8:
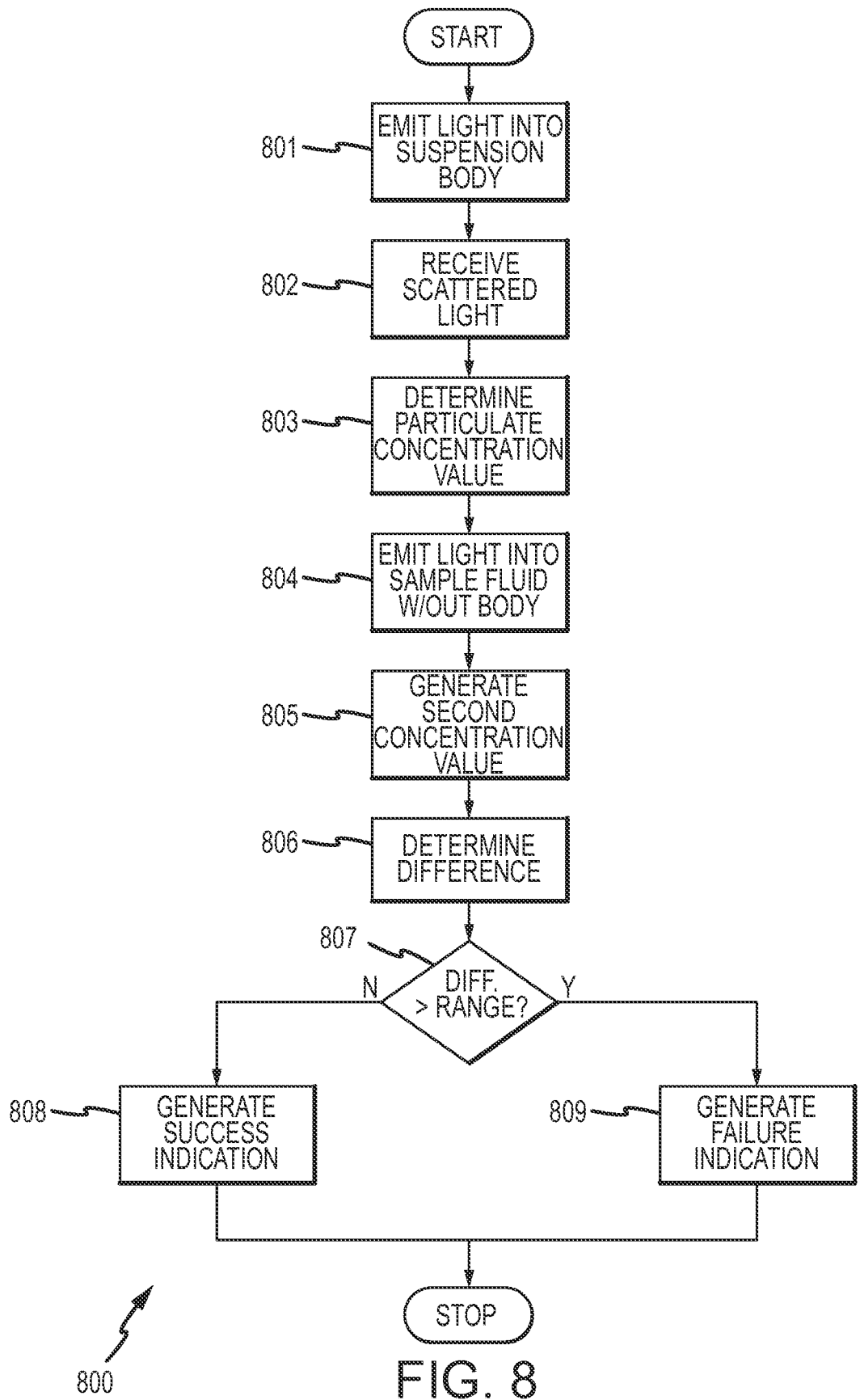
FIG. 8 is a flowchart of a verification method for an optical particulate measurement instrument according to an embodiment of the invention.

FIG. 8 is a flowchart 800 of a verification method for an optical particulate measurement instrument according to an embodiment of the invention. In step 801, light is emitted into a sample chamber and into a standard media suspension body, as previously discussed.

In step 802, a light detector receives scattered light that is scattered within the suspension body, as previously discussed.

In step 803, a particulate concentration value is determined from the received scattered light, as previously discussed. The particulate concentration value corresponds to the presence of the suspension body.

In step 804, light is emitted into the sample fluid without the standard media suspension body. The sample fluid is otherwise unchanged.

In step 805, a second concentration value is determined. The second concentration value is determined using scattered light received from the sample fluid without the suspension body. The second concentration value corresponds to the absence of the suspension body.

In step 806, a difference between the particulate concentration value and the second concentration value is determined, as previously discussed.

In step 807, the difference is compared to a predetermined acceptable range, as previously discussed. If the difference is not greater than the predetermined acceptable range, then the method proceeds to step 808. If the difference is greater than the predetermined acceptable range, then the method proceeds to step 809.

In step 808, a success indication is generated, as previously discussed.

In step 809, a failure indication is generated, as previously discussed.

Figure 9:
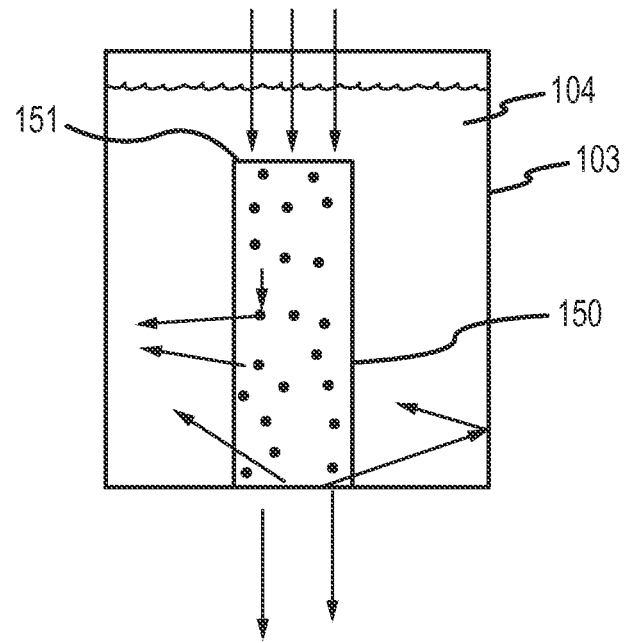
FIG. 9 shows a first standard media suspension body inserted into the sample chamber.

FIG. 9 shows a first standard media suspension body 150 inserted into the sample chamber 103. Using the first standard media suspension body 150, a first light scattering measurement is obtained. In this figure, light not scattered by the first standard media suspension body 150 passes out of the sample chamber 103 (see arrows at the bottom of the figure). In addition, light not scattered by the standard media suspension body 150 can also be scattered by the sample chamber 103. This scattered light can affect the measurements of the light receiver 106 and can degrade the accuracy of the optical particulate measurement instrument 10. A method according to the invention can be used to detect and determine light scattering due to the sample chamber 103 (see FIG. 11 and the accompanying discussion). Two different standard media suspension bodies can be used to determine sample chamber scattering. The first can be the sample body 150 as shown in FIG. 9.

Figure 10:
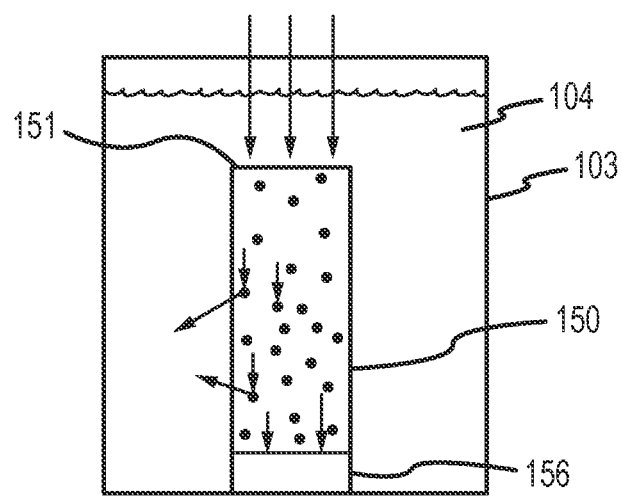
FIG. 10 shows a second standard media suspension body inserted into the sample chamber, with the second standard media suspension body including an end cap.

FIG. 10 shows a second standard media suspension body 150 inserted into the sample chamber 103, with the second standard media suspension body 150 including the end cap 156. Using the second standard media suspension body 150, a second light scattering measurement is obtained. The two measurements should be the same if the sample chamber 103 is not scattering light toward the light receiver 106. However, if the sample chamber 103 is scattering an undesirable amount of light, the second measurement should be less than the first measurement, as the end cap 156 will prevent light from being scattered by the sample chamber 103. The two measurements can therefore be compared in order to determine the amount of light being scattered by the sample chamber 103.

Figure 11:
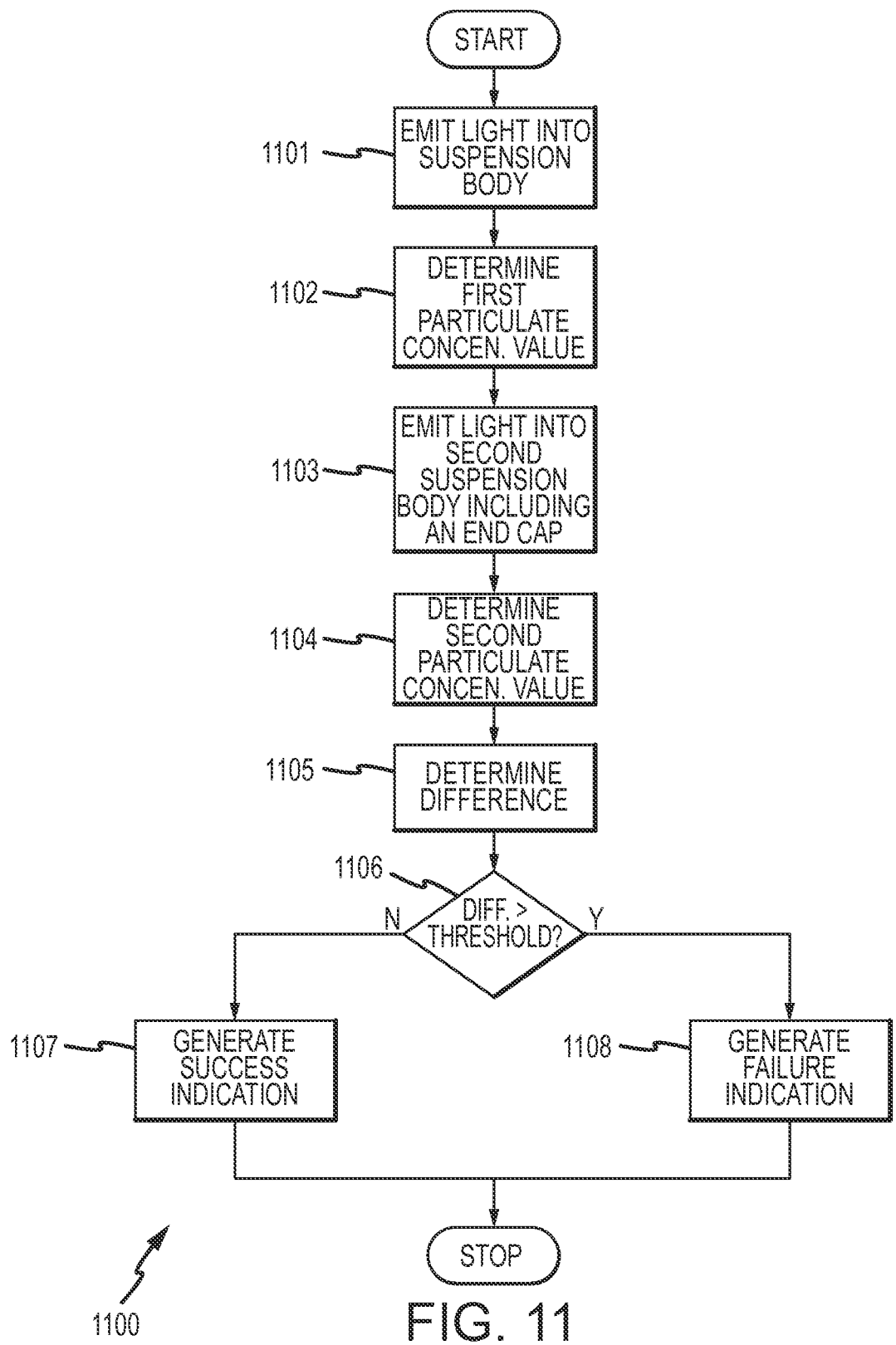
FIG. 11 is a flowchart of a verification method for an optical particulate measurement instrument according to an embodiment of the invention.

FIG. 11 is a flowchart 1100 of a verification method for an optical particulate measurement instrument according to an embodiment of the invention. In step 1101, first light is emitted into a sample chamber and into a first standard media suspension body 150. The first standard media suspension body does not include any end cap. Consequently, the emitted light can be potentially scattered by the sample chamber 103 as the first light exits the first standard media suspension body 150.

In step 1102, a first particulate concentration value is determined from the received first scattered light. The first particulate concentration value is determined by a light receiver in the instrument. The first particulate concentration value corresponds to the presence of the suspension body and comprises a measurement/quantification of light scattered by the suspension body. The first particulate concentration value can also include light scattered by the sample chamber 103 as the first light exits the first standard media suspension body 150.

In step 1103, second light is emitted into the sample fluid and into a second standard media suspension body 150. The second standard media suspension body 150 includes an end cap 156 that substantially absorbs impinging light. As a result, the sample chamber 103 cannot scatter light.

In step 1104, a second particulate concentration value is determined from the received second scattered light. The second particulate concentration value corresponds to the presence of the second standard media suspension body 150 and comprises a measurement/quantification of light scattered by just the second standard media suspension body 150. The second particulate concentration value does not include light scattered by the sample chamber.

In step 1105, a difference between the first particulate concentration value and the second particulate concentration value is determined.

In step 1106, the difference is compared to a predetermined chamber scattering threshold. If the difference does not exceed the predetermined chamber scattering threshold, then the method proceeds to step 1107. If the difference is greater than the predetermined chamber scattering threshold, then the method proceeds to step 1108.

In step 1107, a success indication is generated. In some embodiments, the success indication comprises an indication that the scattering of light by the sample chamber 103 is below the threshold. This may indicate that the sample chamber 103 is acceptably clean, for example.

In step 1108, a failure indication is generated. In some embodiments, the failure indication comprises an indication that the scattering of light by the sample chamber 103 exceeds the predetermined chamber scattering threshold. This may indicate a need to service the sample chamber 103 or the optical particulate measurement instrument 10.

The suspension body, instrument, and method according to some embodiments can be used insitu and without removal of the sample fluid. The suspension body, instrument, and method according to some embodiments can further be employed without the need for any precision alignment of the standard. The suspension body, instrument, and method according to some embodiments can be used without the need for a pre-servicing prior to verification.

The suspension body, instrument, and method according to some embodiments provide a means to assess the operational performance and functionality of a turbidimeter, nephelometer or other optical particulate measurement instrument. The suspension body, instrument, and method according to some embodiments can be used to provide a determination of a reading accuracy, a change in performance, or an operational failure since a last standard calibration was performed.

The suspension body, instrument, and method according to some embodiments can provide a verification capability. The suspension body, instrument, and method according to some embodiments can provide a verification capability that eliminates alignment and positioning difficulties. The suspension body, instrument, and method according to some embodiments can provide a verification capability that is not affected by movement of the instrument, that is quick and easy to perform, and that can be performed in the field.

I claim:

1. A standard media suspension body adapted for verification of an optical particulate measurement instrument comprising:
   a substantially solid three-dimensional outer surface configured to be at least partially immersed in a sample fluid of water and including a first end and a second end disposed along an axis of illumination A and at least one outer surface extending between the first end and-the second end, with the first end being configured to admit light into the standard media suspension body;
   an inner volume, with at least a portion of the inner volume including a substantially suspended light scattering material that is configured to scatter a predetermined quantum of the admitted light; and
   an end cap formed on the second end and comprising a light absorbing material, wherein light exiting the second end is substantially absorbed by the end cap.

2. The suspension body of claim 1, with the standard media suspension body including a refractive index that substantially matches a sample fluid refractive index.

3. The suspension body of claim 1, with the standard media suspension body further comprising:
   a substantially solid body of suspension material; and
   light scattering material held in suspension by the solid suspension material.

4. The suspension body of claim 1, with the standard media suspension body further comprising:
   a substantially solid body of suspension material; and
   amorphous and non-amorphous molecular bonds in at least a portion of the suspension material.

5. The suspension body of claim 1, with the standard media suspension body further comprising:
   a substantially solid body of suspension material; and
   bubbles distributed through at least a portion of the suspension material.

6. The suspension body of claim 1, with the standard media suspension body further comprising:
   an outer shell; and
   a suspension material held in the outer shell, with the suspension material including the suspended light scattering material.

7. The suspension body of claim 6, with the suspension material comprising a suspension liquid, a suspension gel, a semisolid, or other settable liquid contained within the outer shell.

8. The suspension body of claim 1, with the standard media suspension body further comprising:
   a first optical surface at the first end of the standard media suspension body for admitting the impinging light entering the standard media suspension body;
   a third optical surface at the second end for the transmittance of unscattered light propagating substantially through and exiting the standard media suspension body substantially along the axis of illumination A; and
   a second optical surface extending at least partially between the first end and the second end for the transmittance of scattered light exiting from the standard media suspension body substantially perpendicularly to the axis of illumination A;
   with the first end polished to form the first optical surface, the second end polished to form the third optical surface, with the first end and the second end disposed along the axis of illumination A, and at least a portion of an outer surface between the first end and the second end being polished to form the second optical surface.

9. An optical particulate measurement instrument, comprising:
   a light source positioned to emit light into a test chamber along an axis of illumination A;
   a light receiver positioned at least partially in the test chamber and positioned to receive light along a light scattering path;
   a substantially open sample chamber positioned at a juncture of the axis of illumination A and the light scattering path, with the sample chamber configured to hold a sample fluid for measurement; and
   a standard media suspension body at least partially immersed in the sample fluid of water in the sample chamber, with the standard media suspension body being removable and being configured to scatter a predetermined quantum of the admitted light corresponding to a turbidity standard;
   wherein the optical particulate measurement instrument is configured to emit the light into the standard media suspension body, receive the scattered light that is scattered by the standard media suspension body and that has passed through at least some of the sample fluid, and perform a verification of the optical particulate measurement instrument using the scattered light.

10. The instrument of claim 9, wherein the optical particulate measurement instrument is configured to emit light into the standard media suspension body, receive scattered light that is scattered by the standard media suspension body and that has passed through at least some of the sample fluid, determine a particulate concentration value using the received scattered light, determine a difference between the particulate concentration value and a reference value, compare the difference to a predetermined tolerance range, generate a verification success indication if the difference is within the predetermined tolerance range, and generate a verification failure indication if the difference is outside the predetermined tolerance range.

11. The instrument of claim 9, with the optical particulate measurement instrument being further configured to emit light into the standard media suspension body, receive the scattered light, determine a particulate concentration value using the received scattered light, emit light into the sample fluid in the sample chamber without the standard media suspension body, generate a second concentration value without the standard media suspension body, determine a difference between the particulate concentration value and the second concentration value, compare the difference to a predetermined tolerance range, generate a verification success indication if the difference is within the predetermined tolerance range, and generate a verification failure indication if the difference is outside the predetermined tolerance range.

12. The instrument of claim 9, with the standard media suspension body comprising:
   a substantially solid three-dimensional outer surface including a first end and a second end disposed along an axis of illumination A and at least one outer surface extending between the first end and the second end, with the first end being configured to admit the impinging light; and
   an inner volume, with at least a portion of the inner volume including a substantially suspended light scattering material that is configured to scatter the predetermined quantum of the admitted light received from a light source out of the at least one outer surface.

13. The instrument of claim 9, with the standard media suspension body comprising:
- a substantially solid three-dimensional outer surface including a first end and a second end disposed along an axis of illumination A and at least one outer surface extending between the first end and the second end, with the first end being configured to admit the impinging light;
- an inner volume, with at least a portion of the inner volume including a substantially suspended light scattering material that is configured to scatter the predetermined quantum of the admitted light received from a light source out of the at least one outer surface; and
- an end cap formed on the second end and comprising a light absorbing material, wherein light exiting the second end is substantially absorbed by the end cap.

14. A verification method for an optical particulate measurement instrument, comprising:
- emitting light into a removable standard media suspension body at least partially immersed in a sample fluid of water held in a substantially open sample chamber of the optical particulate measurement instrument, with the standard media suspension body being configured to scatter a predetermined quantum of the admitted light corresponding to a turbidity standard;
- receiving scattered light that is scattered by the standard media suspension body and that has passed through at least some of the sample fluid; and
- performing a verification of the optical particulate measurement instrument using the scattered light 15. The method of claim 14, wherein the standard media suspension body is three-dimensional.

16. The method of claim 14, wherein the standard media suspension body is substantially fully immersed in the sample fluid.

17. The method of claim 14, with the standard media suspension body including a refractive index that substantially matches a sample fluid refractive index.

18. The method of claim 14, with performing the verification further comprising:
- determining a particulate concentration value using the received scattered light;
- determining a difference between the particulate concentration value and a reference value;
- comparing the difference to a predetermined tolerance range; and
- generating a verification success indication if the difference is within the predetermined tolerance range.

19. The method of claim 14, with performing the verification comprising:
- determining a particulate concentration value using the received scattered light;
- emitting light into the sample fluid in the sample chamber without the standard media suspension body;
- generating a second concentration value without the standard media suspension body;
- determining a difference between the particulate concentration value and the second concentration value;
- comparing the difference to a predetermined tolerance range; and
- generating a verification success indication if the difference is within the predetermined tolerance range.

* * * * *